(12) United States Patent
Harris et al.

(10) Patent No.: US 10,713,694 B1
(45) Date of Patent: Jul. 14, 2020

(54) SYSTEMS AND METHODS FOR DETERMINING PRODUCT PRICING FOR PRODUCTS IN A HEALTHCARE TRANSACTION

(71) Applicant: McKesson Corporation, Irving, TX (US)

(72) Inventors: Patrick Harris, Atlanta, GA (US); William Turner, Overland Park, KS (US)

(73) Assignee: McKesson Corporation, Irving, TX (US)

( * ) Notice: Subject to any disclaimer, the term of this patent is extended or adjusted under 35 U.S.C. 154(b) by 777 days.

(21) Appl. No.: 14/466,995

(22) Filed: Aug. 23, 2014

(51) Int. Cl.
*G06Q 30/02* (2012.01)
*G06Q 50/22* (2018.01)
*G06F 19/00* (2018.01)

(52) U.S. Cl.
CPC ....... *G06Q 30/0283* (2013.01); *G06F 19/328* (2013.01); *G06Q 50/22* (2013.01)

(58) Field of Classification Search
CPC .. G06F 19/328; G06F 19/3456; G06F 19/326; G06Q 50/22; G06Q 30/0207; G06Q 30/0206; G06Q 40/00; G06Q 30/04; G06Q 50/24
USPC .......................................................... 705/2
See application file for complete search history.

(56) References Cited

U.S. PATENT DOCUMENTS

| 5,550,734 A | 8/1996 | Tarter et al. |
| 5,628,530 A | 5/1997 | Thornton |
| 6,012,035 A | 1/2000 | Freeman, Jr. et al. |
| 6,208,973 B1 | 3/2001 | Boyer et al. |
| 6,757,898 B1 | 6/2004 | Ilsen et al. |

(Continued)

FOREIGN PATENT DOCUMENTS

| CA | 2482370 | 3/2006 |
| WO | 1995003569 | 2/1995 |

(Continued)

OTHER PUBLICATIONS

Final Office Action for U.S. Appl. No. 14/173,200 dated Jun. 13, 2016.

(Continued)

*Primary Examiner* — Victoria P Augustine
*Assistant Examiner* — Teresa S Williams
(74) *Attorney, Agent, or Firm* — Alston & Bird LLP

(57) ABSTRACT

Systems and methods are provided for determining and communicating proper pricing information and other pre- and post-adjudication information, such as an availability of a lower price for a prescription, as part of the processing of a healthcare transaction. A healthcare transaction, such as a healthcare claim transaction, may be received by the service provider computer from a pharmacy computer. The service provider computer may determine if an adjudication platform is available for the prescribed product. The service provider computer may generate a modified healthcare claim transaction and transmit the modified healthcare claim transaction to a claims processor computer for adjudication. The service provider computer may receive an approved adjudicated claim transaction response and perform any post-adjudication on the response. The approved adjudicated claim transaction response may be transmitted to the pharmacy.

16 Claims, 6 Drawing Sheets

(56) References Cited

U.S. PATENT DOCUMENTS

| | | | |
|---|---|---|---|
| 6,769,228 B1 | 8/2004 | Mahar | |
| 7,155,397 B2 | 12/2006 | Alexander et al. | |
| 7,734,483 B1 | 6/2010 | Smith et al. | |
| 8,036,913 B1* | 10/2011 | Pinsonneault | G06F 19/328 705/2 |
| 8,036,918 B1* | 10/2011 | Pinsonneault | G06F 19/328 705/2 |
| 8,060,379 B1 | 11/2011 | Pinsonneault | |
| 8,321,283 B2* | 11/2012 | Rowe, III | G06F 19/328 705/2 |
| 8,326,773 B1* | 12/2012 | Bellamy | G06Q 99/00 705/1.1 |
| 8,392,209 B1* | 3/2013 | Bertha | G06F 19/328 705/2 |
| 8,630,873 B1* | 1/2014 | Wiley, II | G06Q 50/22 705/2 |
| 8,639,523 B1* | 1/2014 | Pinsonneault | G06Q 10/10 705/14.36 |
| 8,671,018 B2* | 3/2014 | Thomas | G06Q 30/02 705/14.25 |
| 9,373,065 B1 | 6/2016 | Hoffman | |
| 2001/0023415 A1 | 9/2001 | Keil | |
| 2002/0002495 A1 | 1/2002 | Ullman | |
| 2002/0087583 A1 | 7/2002 | Morgan et al. | |
| 2002/0095314 A1 | 7/2002 | Bodsworth | |
| 2002/0111832 A1 | 8/2002 | Judge | |
| 2002/0198831 A1 | 12/2002 | Patricelli et al. | |
| 2003/0009367 A1 | 1/2003 | Morrison | |
| 2003/0050799 A1 | 3/2003 | Jay et al. | |
| 2003/0149594 A1* | 8/2003 | Beazley | G06F 19/328 705/2 |
| 2003/0149625 A1 | 8/2003 | Leonardi | |
| 2003/0154163 A1 | 8/2003 | Phillips et al. | |
| 2003/0229540 A1 | 12/2003 | Algeiene | |
| 2003/0236747 A1 | 12/2003 | Sager | |
| 2004/0039599 A1 | 2/2004 | Fralic | |
| 2004/0039691 A1 | 2/2004 | Barrat et al. | |
| 2004/0059600 A1 | 3/2004 | Ball et al. | |
| 2004/0073457 A1 | 4/2004 | Kalies | |
| 2004/0078234 A1 | 4/2004 | Tallal, Jr. | |
| 2004/0117323 A1 | 6/2004 | Mindala | |
| 2004/0139005 A1 | 7/2004 | Mascavage, III | |
| 2004/0148198 A1 | 7/2004 | Kalies | |
| 2004/0249745 A1 | 12/2004 | Baaren | |
| 2005/0015280 A1 | 1/2005 | Gabel et al. | |
| 2005/0060201 A1 | 3/2005 | Connely, III et al. | |
| 2005/0102169 A1 | 5/2005 | Wilson | |
| 2005/0108067 A1 | 5/2005 | Chapman et al. | |
| 2005/0154627 A1 | 7/2005 | Zuzek et al. | |
| 2005/0187793 A1 | 8/2005 | Myles | |
| 2005/0197862 A1 | 9/2005 | Paterson et al. | |
| 2005/0240473 A1 | 10/2005 | Ayers, Jr. et al. | |
| 2005/0288972 A1 | 12/2005 | Marvin et al. | |
| 2006/0020514 A1 | 1/2006 | Yered | |
| 2006/0026041 A1 | 2/2006 | Ullman | |
| 2006/0036470 A1 | 2/2006 | Oaks | |
| 2006/0149595 A1 | 7/2006 | Williams et al. | |
| 2006/0149784 A1 | 7/2006 | Tholl et al. | |
| 2006/0184391 A1 | 8/2006 | Barre et al. | |
| 2006/0206425 A1 | 9/2006 | Sharma | |
| 2006/0212318 A1 | 9/2006 | Dooley et al. | |
| 2006/0259363 A1 | 11/2006 | Jhetam et al. | |
| 2007/0005402 A1 | 1/2007 | Kennedy et al. | |
| 2007/0050209 A1 | 3/2007 | Yered | |
| 2007/0136100 A1 | 6/2007 | Daugherty et al. | |
| 2007/0162303 A1* | 7/2007 | Wiley, II | G06Q 10/10 705/2 |
| 2007/0192206 A1 | 8/2007 | Manesh et al. | |
| 2007/0203750 A1 | 8/2007 | Volchek | |
| 2007/0226009 A1 | 9/2007 | Hicks | |
| 2007/0233525 A1 | 10/2007 | Boyle | |
| 2007/0233526 A1 | 10/2007 | Hoffman et al. | |
| 2007/0239493 A1 | 10/2007 | Sweetland et al. | |
| 2007/0265887 A1 | 11/2007 | McLaughlin et al. | |
| 2008/0097944 A1 | 4/2008 | Kelly et al. | |
| 2008/0183492 A1 | 7/2008 | Warren et al. | |
| 2008/0215370 A1 | 9/2008 | Dent et al. | |
| 2009/0048864 A1 | 2/2009 | Kozlowski et al. | |
| 2009/0055225 A1 | 2/2009 | Russell | |
| 2009/0210286 A1 | 8/2009 | Bisdikian | |
| 2009/0313039 A1* | 12/2009 | Cedergreen | G06Q 30/02 705/2 |
| 2010/0057640 A1* | 3/2010 | Cannata | G06Q 30/0283 705/400 |
| 2010/0241458 A1 | 9/2010 | Hasan | |
| 2012/0035952 A1 | 2/2012 | Coyne | |
| 2012/0253846 A1* | 10/2012 | John | G06Q 30/0207 705/3 |
| 2013/0311389 A1* | 11/2013 | Kaehler | G06Q 10/10 705/322 |
| 2014/0039911 A1 | 2/2014 | Iyer | |
| 2015/0006198 A1 | 1/2015 | Furr et al. | |
| 2015/0220690 A1 | 8/2015 | Kahlon | |
| 2015/0234991 A1 | 8/2015 | Pinsonneault | |
| 2015/0269695 A1 | 9/2015 | Pinsonneault et al. | |
| 2016/0027136 A1* | 1/2016 | Taketomo | G06Q 40/08 705/2 |
| 2018/0018647 A1 | 1/2018 | Fredman et al. | |

FOREIGN PATENT DOCUMENTS

| | | |
|---|---|---|
| WO | 2000039737 | 7/2000 |
| WO | 2007025295 | 3/2007 |

OTHER PUBLICATIONS

Sampson, R.J., Taking Control of Health Care Costs, Best's Review—Life Health Insurance Edition, Nov. 1983, vol. 84, Issue 7, USA; Abstract only.

Anonymous, ACS to Demonstrate Electronic Health Record Solution Suite at MMIS 2007 Conference; EHR Tools Consolidate Data, Provide Useful Information at the Point of Care for Medicaid Providers, Payers, and Patients, PR Newswire, Aug. 13, 2007, New York, NY, USA.

Lamb, J., New Era of Electronic Medicine Management: E-Prescriptions, Britain's Traditionally Cautious National Health Service is Starting Trials for Online Prescription, with the Aim of Cutting Costs. Financial Times, London, Feb. 21, 2001, p. 6, London, United Kingdom.

Anonymous, Pharmacy Industry Leaders Launch Firm to Supply Real-Time Data. PR Newswire. Jul. 30, 2001, p. 1, New York, NY, USA.

Anonymous, Medic; On-line Goes In-House, Chain Store Age Executive, Jan. 1987, vol. 63, Issue 1, USA; Abstract only.

Non-final Office Action for U.S. Appl. No. 12/101,997 dated Dec. 6, 2010.

Final Office Action for U.S. Appl. No. 12/101,997 dated May 9, 2011.

Notice of Allowance for U.S. Appl. No. 12/101,997 dated Sep. 1, 2011.

Non-final office Action for U.S. Appl. No. 14/173,200 dated Dec. 11, 2015.

Anonymous, TechRx Announces Successful Beta Deployment of T-Rex. PR Newswire. May 13, 2002.

Office Action for U.S. Appl. No. 14/811,392 dated Nov. 8, 2018.

Office Action for U.S. Appl. No. 14/811,392 dated Apr. 24, 2019, 15 pages.

Abrams, Lawrene W. "Pharmacy Benefit Managers As Bargaining Agents", Paper presented at the Western Economic Association International, 80th Annual Conference Jul. 6, 2005 San Francisco, the Dec. 10, 2005 entry accessted at http://web.archive.org/web/2005129093448/http://www.nu-retail.com/pbm_bargaining_paper.pdf on Aug. 23, 2011.

* cited by examiner

SYSTEMS AND METHODS FOR DETERMINING PRODUCT PRICING FOR PRODUCTS IN A HEALTHCARE TRANSACTION

TECHNICAL FIELD

Aspects of the disclosure relate generally to healthcare transactions and more particularly to systems and methods for determining proper product pricing and communicating pre- and/or post-adjudication information as part of the processing of a healthcare transaction.

BACKGROUND

Providing pharmacy dispensing systems a method supporting submission of multiple usual and customary charges (U&C) representing multiple prices that may be charged for a product to third parties can be a challenge with today's pharmacy computer systems. For example, pharmacies typically establish a U&C charge that represents a price for a specific drug, for a specific quantity, on a specific day, at a specific pharmacy location. The U&C price is typically defined as the amount charged cash customers for the prescription exclusive of sales tax or other amounts claimed. Because this definition has been adopted by the Health Insurance Portability and Accountability Act (HIPAA), the definition for U&C charges cannot be modified unless a regulatory body redefines it. However, third parties (e.g., Medicaid) develop managed care pricing schema based on the "lower of" price, based upon the notion that any given patient/beneficiary of a policy shall not be forced to pay a higher rate than the price offered by the pharmacy to the general cash paying public.

In an attempt to develop loyalty, pharmacies have established pharmacy loyalty programs or other pharmacy offered pricing levels available to a patient that continues to receive their medication from a specific pharmacy. However, in the current pharmacy environment, a pharmacy typically does not have a system for providing pricing levels (e.g., pharmacy loyalty program) off of an established U&C charge. Rather, the pharmacy may rely on pharmacists to manually coordinate benefits and re-pricing of the product being requested by a customer in the prescription, or the pharmacy may choose to face the possibility of paying a financial penalty and simply not offer discount pricing.

BRIEF DESCRIPTION OF THE DRAWINGS

Reference will now be made to the accompanying drawings, which are not necessarily drawn to scale, and wherein.

DETAILED DESCRIPTION OF EXEMPLARY EMBODIMENTS

Figure 1:
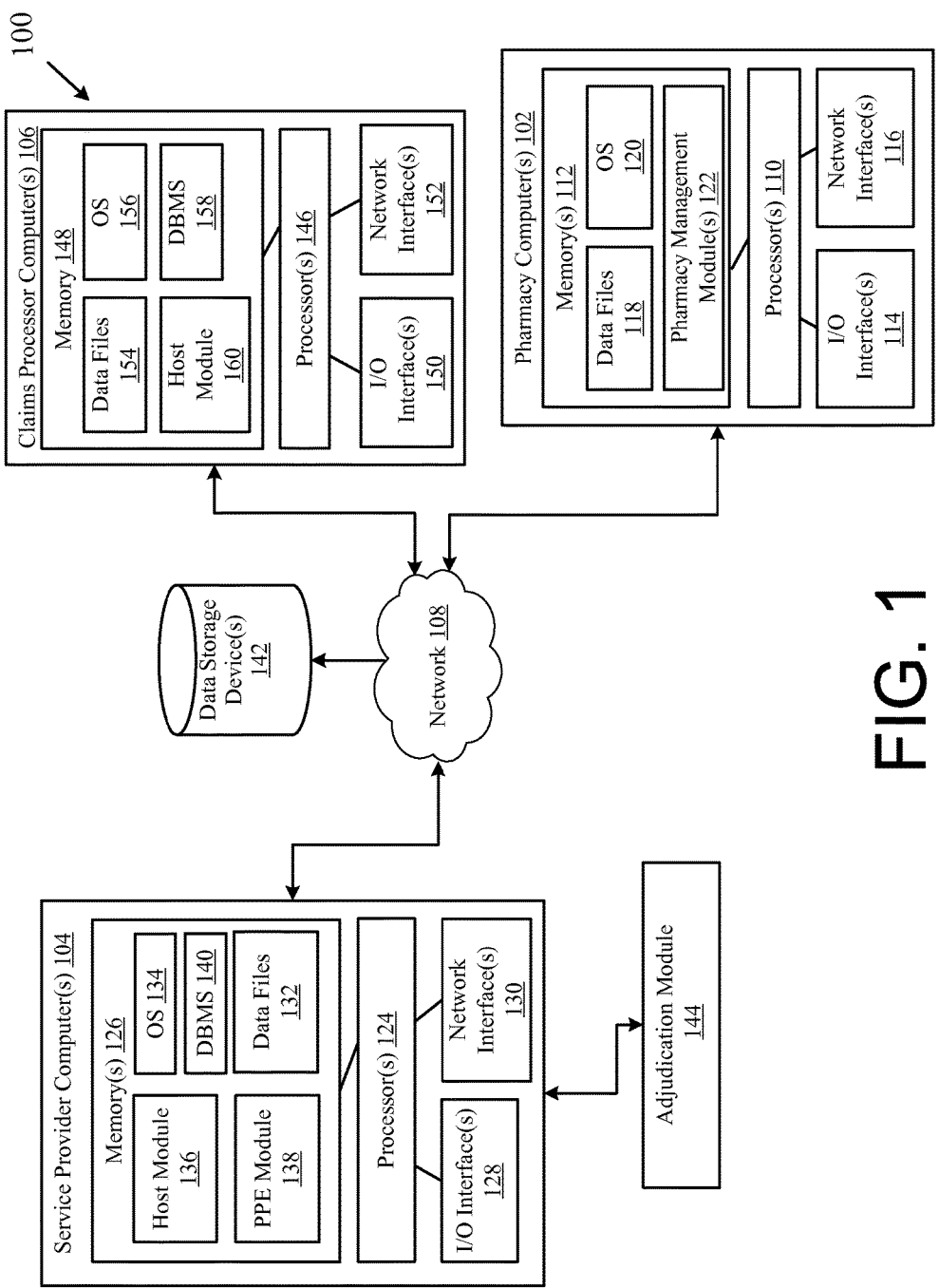
FIG. 1 illustrates an example system for facilitating, among other things, the determination of proper product pricing and the communication of pre-/post-adjudication information to a pharmacy as part of the processing of a healthcare transaction, according to one exemplary embodiment.

Exemplary embodiments will now be described more fully hereinafter with reference to the accompanying drawings, in which exemplary embodiments are shown. The concepts disclosed herein may, however, be embodied in many different forms and should not be construed as limited to the exemplary embodiments set forth herein; rather, these embodiments are provided so that this disclosure will be thorough and complete, and will fully convey the scope of the concepts to those skilled in the art. Like numbers refer to like, but not necessarily the same or identical, elements throughout.

Exemplary embodiments described herein include systems and methods for determining and communicating proper product pricing and other pre- and post-adjudication information, that may be available for a patient. In this regard, the pricing information and the other pre- and/or post-adjudication information may be determined as a part of the processing of a healthcare transaction, such as a predetermination of benefits transaction, healthcare claim transaction, prescription claim or billing request, healthcare order transaction, or e-prescription transaction (e.g., electronic prescription order transaction, e-script, or e-prescription). In some example implementations, a healthcare claim transaction may be communicated from a pharmacy computer to a service provider computer. In one example, the healthcare claim transaction may be a National Council for Prescription Drug Programs (NCPDP) formatted prescription claim request. The service provider computer may determine whether an adjudication platform is available for processing the healthcare claim transaction. If an adjudication platform is available, the service provider may employ the adjudication platform to perform pre- and/or post-adjudication on the healthcare claim transaction to determine proper pricing of the product/medication requested in the transaction.

In one example, the service provider computer may employ or send information to an adjudication module to determine whether an adjudication platform may be available as a part of the processing of a healthcare transaction. The adjudication module may utilize one or more tools to analyze the healthcare transaction. For example, the adjudication module may access one or more pricing schemas based on information (e.g., pharmacy identifiers, product/medication identifiers, etc.), in the healthcare transaction.

The adjudication module may compare information from the one or more pricing schemas with information in the healthcare transaction (e.g., U&C price) to determine, for example, if a lower price for the requested product in the healthcare transaction may be available to the patient and/or payor.

The term "product," and its pluralized form, as used herein, is intended to refer to any good, including a medication, formulation, or other substance. Additionally, it is appreciated that a "medication" or "drug" may be referred to herein for simplicity as being the subject of a healthcare transaction; however, a healthcare transaction may be for any product, good, or service, and is not intended to be limited to drugs.

System Overview

FIG. 1 illustrates an example system 100 for facilitating, among other things, the determination of proper product pricing and the communication of pre-/post-adjudication information to a pharmacy as part of the processing of a healthcare transaction. As shown in FIG. 1, the system 100 may include one or more pharmacy computers 102, service provider computers 104, and/or claims processor computers 106. As desired, each of the pharmacy computers 102, service provider computers 104, and/or claims processor computers 106 may include one or more processing devices that may be configured for accessing and reading associated computer-readable media having stored data thereon and/or computer-executable instructions for implementing various embodiments of the disclosure.

Generally, network devices and systems, including one or more pharmacy computers 102, service provider computers 104, and/or claims processor computers 106, may include or otherwise be associated with suitable hardware and/or software for transmitting and receiving data and/or computer-executable instructions over one or more communication links or networks. These network devices and systems may also include any number of processors for processing data and executing computer-executable instructions, as well as other internal and peripheral components currently known in the art or which may be developed in the future. Further, these network devices and systems may include or be in communication with any number of suitable memory devices operable to store data and/or computer-executable instructions. By executing computer-executable instructions, each of the network devices may form a special-purpose computer or particular machine. As used herein, the term "computer-readable medium" describes any medium for storing computer-executable instructions.

As shown in FIG. 1, the one or more pharmacy computers 102, service provider computers 104, and/or claims processor computers 106 may be in communication with each other via one or more networks, such as network 108, which may include one or more independent and/or shared private and/or public networks including the Internet or a publicly switched telephone network. In other example embodiments, one or more components of the system 100 may communicate via direct connections and/or communication links. Each of these components—the pharmacy computer 102, service provider computer 104, claims processor computer 106, and the network 108—will now be discussed in further detail. Although the components are generally discussed as singular components, as may be implemented in various example embodiments, in alternative exemplary embodiments each component may include any number of suitable computers and/or other components.

With continued reference to FIG. 1, any number of pharmacy computers 102 may be associated with (e.g., located at and/or providing services for) any number of pharmacies and/or pharmacists. Each pharmacy computer 102 may be any suitable processor-driven device that facilitates communicating, processing, and/or fulfilling healthcare transactions such as predetermination of benefits requests, healthcare claim transactions, prescription claim or billing requests, healthcare order transactions, or e-prescription transactions (e.g., electronic prescription order transactions, e-scripts, or e-prescriptions) received from or communicated to the service provider computer 104. For example, a pharmacy computer 102 may be a processor-driven device associated with (e.g., located within or providing computing services for) a pharmacy. As desired, the pharmacy computer 102 may include any number of special-purpose computers or other particular machines, application-specific integrated circuits, microcontrollers, personal computers, minicomputers, mainframe computers, servers, and the like. In certain example embodiments, the operations of the pharmacy computers 102 may be controlled by computer-executed or computer-implemented instructions that are executed by one or more processors associated with the pharmacy computers 102 to form a special-purpose computer or other particular machine that is operable to facilitate the receipt, generation, and/or fulfillment of healthcare transactions (e.g., predetermination of benefits requests, healthcare claim transactions, prescription claim or billing requests, healthcare order transactions, or e-prescription transactions (e.g., electronic prescription order transactions, e-scripts, or e-prescriptions)). The one or more processors that control the operations of a pharmacy computer 102 may be incorporated into the pharmacy computer 102 and/or may be in communication with the pharmacy computer 102 via one or more suitable networks. In certain example embodiments, the operations and/or control of the pharmacy computers 102 may be distributed among several processing components.

Similar to other components of the system 100, each pharmacy computer 102 may include one or more processors 110, one or more memory devices 112, one or more input/output (I/O) interfaces 114, and one or more network interfaces 116. The one or more memory devices 112 may be any suitable memory devices, for example, caches, read-only memory device, random access memory devices, magnetic storage devices, removable memory devices, etc. The one or more memory devices 112 may store data, executable instructions, and/or various program modules utilized by the pharmacy computers 102, for example, data files 118, an operating system (OS) 120, and a pharmacy management module 122. The data files 118 may include any suitable information that is utilized by the pharmacy computer 102. The OS 120 may be a suitable software module that controls the general operation of the pharmacy computer 102. The OS 120 may also facilitate the execution of other software modules by the one or more processors 110. The OS 120 may be any operating system known in the art or which may be developed in the future including, but not limited to, Microsoft Windows®, Apple OSX™, Linux, Unix, Apple iOS™, Google Android™, or a mainframe operating system.

The one or more I/O interfaces 114 may facilitate communication between the pharmacy computer 102 and one or more input/output devices, for example, one or more user interface devices, such as a display, keypad, control panel, touch screen display, remote control, microphone, etc., that facilitate user interaction with the pharmacy computer 102. The one or more network interfaces 116 may facilitate connection of the pharmacy computer 102 to one or more suitable networks, for example, the network 108 illustrated in FIG. 1. In this regard, the pharmacy computer 102 may receive adjudicated healthcare transaction responses and/or other communications from the service provider computer 104 and the pharmacy computer 102 may communicate healthcare transactions and information associated with processing healthcare transactions to the service provider computer 104.

The pharmacy management module 122 may be a software application(s), including a dedicated program, for generating and/or fulfilling healthcare transaction orders, reading and/or updating medical records (e.g., prescription records), facilitating patient billing, etc., as well as interacting with the service provider computer 104. For example, a pharmacist or other pharmacy employee, may utilize the pharmacy management module 122 in filling a prescription, recording and/or updating a patient's medical prescription history, and billing, preparing and transmitting a healthcare transaction to the service provider computer 104. Furthermore, the pharmacy computer 102 may utilize the pharmacy management module 122 to retrieve or otherwise receive data, messages, or responses from the service provider computer 104 and/or other components of the system 100.

With continued reference to FIG. 1, one or more service provider computers 104 may be associated with a service provider. In certain exemplary embodiments, the service provider computer 104 may be a switch/router or switch computer that receives and routes healthcare transactions and/or other healthcare requests. For example, the service provider computer 104 may route healthcare transactions, such as a predetermination of benefits transaction, healthcare claim transaction, prescription claim or billing request, healthcare order transaction, or e-prescription transaction (e.g., electronic prescription order transaction, e-script, or e-prescription), communicated from the pharmacy computer 102 to a claims processor computer 106, such as a pharmacy benefits manager (PBM), a healthcare insurer, a Medicare payor, a Medicaid payor, other governmental payor, or other third-party payor. The service provider computer 104 may include, but is not limited to, any suitable processor-driven device that is configured for receiving, processing, assessing and modifying the healthcare transactions from the pharmacy computer 102 relating to prescription information including, but not limited to, medications, medication identifiers (e.g., medication name(s), National Drug Code(s) (NDC number) and RxNorm medication identifiers), quantity of medication to be dispensed, patient information (e.g., patient name, patient address, patient gender, patient date of birth), and/or prescription profitability information for a medication identified in the healthcare transaction. Any number of pharmacy computers 102, and/or claims processor computers 106 may be in communication with the service provider computer 104 as desired in various example embodiments.

The service provider computer 104 may include any number of special-purpose computers or other particular machines, application-specific integrated circuits, microcontrollers, personal computers, minicomputers, mainframe computers, servers, networked computers, and/or other processor-driven devices. In certain example embodiments, the operations of the service provider computer 104 may be controlled by computer-executed or computer-implemented instructions that are executed by one or more processors associated with the service provider computer 104 to form a special-purpose computer or other particular machine that is operable to facilitate the receipt, routing, modification, and/or processing of healthcare transactions. The one or more processors that control the operations of the service provider computer 104 may be incorporated into the service provider computer 104 and/or may be in communication with the service provider computer 104 via one or more suitable networks. In certain example embodiments, the operations and/or control of the service provider computer 104 may be distributed among several processing components.

Similar to the pharmacy computer 102, the service provider computer 104 may include one or more processors 124, one or more memory devices 126, one or more input/output ("I/O") interfaces 128, and one or more network interfaces 130. The one or more memory devices 126 may be any suitable memory device, for example, caches, read-only memory devices, random access memory devices, magnetic storage devices, removable storage devices, etc. The one or more memory devices 126 may store data, executable instructions, and/or various program modules utilized by the service provider computer 104, for example, data files 132, an operating system ("OS") 134, a host module 136, a pre- and post-edit (PPE) module 138, and a database management system (DBMS) 140 to facilitate management of data files 132 and other data stored in the memory devices 126 and/or one or more databases 142. The OS 134 may be any operating system known in the art or which may be developed in the future including, but not limited to, Microsoft Windows®, Apple OSX™, Linux, Unix, Apple iOS™, Google Android™, or a mainframe operating system. The OS 134 may be a suitable software module that controls the general operation of the service provider computer 104 and/or that facilitates the execution of other software modules.

The PPE module 138 may be operable to perform one or more pre-edits on a received healthcare transaction, such as predetermination of benefits requests, healthcare claim transactions, prescription claim or billing requests, healthcare order transactions, or e-prescription transactions (e.g., electronic prescription order transactions, e-scripts, or e-prescriptions), prior to routing or otherwise communicating the received healthcare transaction to a suitable claims processor computer 108. Additionally, the PPE module 138 may be operable to perform one or more post-edits on an adjudicated response that is received from a claims processor computer 106 for a healthcare transaction prior to routing the adjudicated response to the pharmacy computer 102. A wide variety of different pre-edits and/or post edits may be performed as desired in various embodiments of the disclosure.

An adjudication module 144 or an adjudication application may also be operative with the service provider computer 104. The adjudication module 144 may include computer-executable instructions operable for performing any pre- and/or post-adjudication as part of the processing of the healthcare transaction. The adjudication module 144 may facilitate many operations including, but not limited to, receipt of eligibility verification, formulary design, and/or pricing schemas consistent with one or more pharmacy pricing levels for one or more medications and/or products, such as, for example, a pharmacy loyalty program requirement. The adjudication module 144 may be implemented as computer-implemented instructions of the memory 126 of the service provider computer 104. Alternatively, the adjudication module 144 may also be implemented as computer-implemented instructions of a memory of a separate computing entity or processor-based system, according to an example embodiment of the disclosure.

The pricing schema may include the cost to the pharmacy associated with the pharmacy computer 102 to acquire a particular medication or product. The pricing schema may be, for example, a cost to acquire a product or medication on a per dosage basis (e.g., a per pill cost), or may be a cost to acquire a particular number of days' supply of the product or medication (e.g., a 30 day supply, a 60 day supply, a 90 day supply, etc.). The pricing schema may further include without limitation, pharmacy level discounts set by a pharmacy or pharmacy chain that the pharmacy belongs to (e.g., includes a franchisee) that are or may be applied to the purchase of a product or medication. A pharmacy level discount may include, for example, a pharmacy loyalty program (e.g., a rewards program). The pharmacy loyalty program may offer one or more discounts (e.g., 5% off, 10% off, or another predetermined percentage or specific monetary amount off for members of the pharmacy loyalty program) on a medication and/or product price. The adjudication module 144 may facilitate storage of data included in the pricing schema in one or more suitable databases and/or data storage devices, such as database 142.

In one example, the adjudication module 144 may communicate to the service provider computer 104 and/or the pharmacy computer 102 a determination of eligibility verification. For example, the adjudication module 144 may verify that a pharmacy associated with a pharmacy computer 102 and/or a claims processor associated with a claims processor computer 106 is eligible for use with the adjudication module 144. In one non-limiting example, the adjudication module 144 may receive a healthcare transaction from the pharmacy computer 102 and/or the service provider computer 104. The adjudication module 144 may access one or more databases, for example databases 142, to access one or more eligibility verification files to determine whether a pharmacy identifier in the received healthcare transaction matches a pharmacy identifier for a pharmacy (e.g., a pharmacy or member of a pharmacy chain that has contracted or otherwise agreed to receive product/medication pricing verification services provided by the adjudication module 144). In addition, the adjudication module 144 may access one or more databases, for example databases 142, to access one or more eligibility verification files to determine whether a Banking Identification Number (BIN number), BIN number and Processor Control Number (PCN), or BIN number and Group ID in the received healthcare transaction match the BIN number, BIN number and PCN, or BIN number and Group ID of a qualified claims processor. In one example, a qualified claims processor may include a payor (e.g., Medicaid, Medicare, third-party payor, etc) that has contracted and or otherwise agreed to receive pre- and/or post-adjudication services (e.g., product/medication pricing verification services). If matches exist and the pharmacy and claims process are determined to be qualified, the eligibility verification may enable the healthcare transaction for subsequent processing by the system 100 described in FIG. 1.

In addition, the adjudication module 144 may be further operable to communicate a response to the pharmacy computer 106. The response, in one example, may include, without limitation, a price associated with a medication and/or product. The price may be different from a U&C price presented in the received healthcare transaction, such as a healthcare claim transaction. For example, the adjudication module 144 may access one or more pricing schemas for the pharmacy from which the healthcare transaction was received. The adjudication module may compare the pricing information within the pricing schema to a U&C charge included in a healthcare claim transaction to determine if a lower price for a medication and/or product may be available to a patient and/or payor. In one example, the pricing schema may include pricing levels corresponding to a pharmacy offered loyalty program, where the loyalty program offers a percentage (e.g., 5%, 10%, 20%, etc.) off of a U&C price. The adjudication module 144 may replace the medication and/or product U&C cost in the U&C cost field in the healthcare claim transaction with the identified lower price. In one example, the response may be communicated to the service provider 104 as a part of the received healthcare transaction. For example, the healthcare transaction may be edited to include the lower price for the medication and/or product and communicated to the service provider 104. In another non-limiting example, the adjudication module 144 may also transmit a message to the pharmacy computer 102 and/or the service provider computer 104 communicating an indication of an availability or non-availability of a lower price.

In certain example embodiments, the adjudication module 144 and/or the service provider computer 104 may be operable to generate one or more invoices or reports associated with the processed healthcare transactions. For example, a modification report may be generated. A modification report may include one or more modifications made to a healthcare transaction and/or an adjudicated response. A wide variety of different types of invoices or reports may be generated as desired in various embodiments of the disclosure. Invoices or reports may be sorted or formatted utilizing a wide variety of different criteria, parameters, and/or techniques. Additionally, the adjudication module 144 and/or the service provider computer 104 may communicate or direct the communication of generated invoices or reports to one or more other components of the system.

A wide variety of different techniques and/or software programs may be utilized to format a generated invoice and/or report. For example, an invoice or report may be formatted as a comma-separated-value (CSV) file, as a spreadsheet file, as a word processor file, as a text file, etc. Additionally, a wide variety of different communication techniques may be utilized to communicate a report to the recipient, including but not limited to, electronic transaction requests, email, short message service messaging, other electronic communications, paper mail, etc. An invoice report may be pushed to a recipient by the adjudication module 144 or other reporting module, or alternatively pulled from the adjudication module 144 by a recipient submitting a request for one or more invoices or reports. Additionally, in certain embodiments, a report may be made available for download from an appropriate web site or server, such as a web site hosted by the service provider computer 104.

According to an example embodiment, the data files 142 may store healthcare transaction records associated with communications received from various pharmacy computers 106, and/or various claims processor computers 108. The data files 142 may also store any number of suitable routing tables that facilitate determining the destination of communications received from a pharmacy computer 102 and/or a claims processor computer 106.

The service provider computer 104 may include additional program modules for performing other processing methods described herein. Those of ordinary skill in the art will appreciate that the service provider computer 104 may include alternate and/or additional components, hardware, or software without departing from the scope of the disclosure.

With continued reference to the service provider computer 104, the one or more I/O interfaces 128 may facilitate communication between the service provider computer 104 and one or more input/output devices, for example, one or more user interface devices, such as a display, keypad, control panel, touch screen display, remote control, microphone, etc., that facilitate user interaction with the service provider computer 104. The one or more network interfaces 130 may facilitate connection of the service provider computer 104 to one or more suitable networks, for example, the network 108 illustrated in FIG. 1. In this regard, the service provider computer 104 may communicate with other components of the system 100, such as the pharmacy computers 102, the claims processor computers 106 and the database 142.

With continued reference to FIG. 1, each of the claims processor computers 106 may be any suitable processor-driven device that facilitates receiving processing (e.g., adjudicating), and/or responding to healthcare transactions received from the service provider computer 104. For example, the claims processor computer 106 may be a processor-driven device associated with a claims processor (e.g., Pharmacy Benefits Manager (PBM), claims payor, healthcare insurance company, Medicaid, Medicare or other government healthcare insurance payor, Medicare Part D provider, claims clearinghouse, etc.). As desired, the claims processor computer 106 may include any number of special purpose computers or other particular machines, application specific circuits, microcontrollers, personal computers, minicomputers, mainframe computers, servers, and the like. In certain embodiments, the operations of the claims processor computer 106 may be controlled by computer-executed or computer-implemented instructions that are executed by one or more processors associated with the claims processor computer 106 to form a special purpose computer or other particular machine that is operable to facilitate the receipt, processing, and/or responding to healthcare transactions received from the service provider computer 104. The one or more processors that control the operations of the claims processor computer 106 may be incorporated into the claims processor computer 106 and/or in communication with the claims processor computer 106 via one or more suitable networks. In certain example embodiments of the disclosure, the operation and/or control of the claims processor computer 106 may be distributed amongst several processing components. In an alternate embodiment, the functions of the claims processor computer may be incorporated into the service provider computer 104.

Similar to other components of the system 100, the claims processor computer 108 may include one or more processors 146, one or more memory devices 148, one or more input/output (I/O) interfaces 150, and one or more network interfaces 152. The memory 148 may be any suitable memory devices, for example, caches, read only memory devices, random access memory devices, magnetic storage devices, removable memory devices, etc. The one or more memory devices 148 may store data, executable instructions, and/or various program modules utilized by the claims processor computer 106, for example, data files 154, an operating system (OS) 156, a database management module (DBMS) 158, and a host module 160. The data files 154 may include any suitable information that is utilized by the claims processor computer 106 to process healthcare transactions, for example, patient profiles, patient insurance information, other information associated with a patient, information associated with a healthcare provider, etc. The OS 156 may be a suitable software module that controls the general operation of the claims processor computer 106. The OS 156 may also facilitate the execution of other software modules by the one or more processors 146, for example the DBMS 158 and/or the host module 160. The OS 156 may be any operating system known in the art or which may be developed in the future including, but not limited to, Microsoft Windows®, Apple OSX™, Linux, Unix, Apple iOS™, Google Android™, or a mainframe operating system. The DBMS 158 may be a suitable software module that facilitates access and management of one or more databases that are utilized to store information that is utilized by the claims processor computer 106 in various embodiments of the disclosure. The host module 160 may initiate, receive, process, and/or respond to requests, such as healthcare transactions, from the host module 160 of the service provider computer 104. The claims processor computer 106 may include additional program modules for performing other pre-processing or post-processing methods described herein. Those of ordinary skill in the art will appreciate that the claims processor computer 106 may include alternate and/or additional components, hardware or software without departing from example embodiments of the disclosure.

The I/O interface(s) 150 may facilitate communication between the processors 146 and various I/O devices, such as a keyboard, mouse, printer, microphone, speaker, monitor, bar code reader/scanner, RFID reader, and the like. The one or more network interface(s) 152 may facilitate connection of the claims processor computer 106 to one or more suitable networks, for example, network 108 illustrated in FIG. 1. In this regard, the claims processor computer 106 may receive healthcare transactions and/or other communication from the service provider computer 104, and the claims processor computer 106 may communicate information associated with the processing and adjudication of the healthcare transactions to the service provider computer 104.

The network 108 may include any telecommunications and/or data network, whether public, private, or a combination thereof, including a local area network, a wide area network, an intranet, the Internet, intermediate handheld data transfer devices, and/or any combination thereof and may be wired and/or wireless, or any combination thereof. The network 108 may also allow for real time, offline, and/or batch transactions to be transmitted between or among the pharmacy computer 102, the service provider computer 104 (including the adjudication module 144), the claims processor computer 106, and the database 142. Various methodologies as described herein, may be practiced in the context of distributed computing environments. Although the service provider computer 104 is shown for simplicity as being in communication with the pharmacy computer 102, the claims processor computer 106, or the database 142 via one intervening network 108, it is to be understood that any other network configurations are possible. For example, intervening network 108 may include a plurality of networks, each with devices such as gateways and routers for providing connectivity between or among the components of the system 100. Instead of or in addition to the network 108, dedicated communication links may be used to connect various devices in accordance with an example embodiment. For example, the service provider computer 104 may form the basis of network 108 that interconnects the pharmacy computer 102, the service provider computer 104 (including the adjudication module 144), the claims processor computer 106, and the database 142.

Those of ordinary skill in the art will appreciate that the system 100 shown in and described with respect to FIG. 1 is provided by way of example only. Numerous other operating environments, system architectures, and device and network configurations are possible. Other system embodiments can include fewer or greater numbers of components and may incorporate some or all of the functionality described with respect to the system components shown in FIG. 1. For example, in an exemplary embodiment, the service provider computer 104 (or other computer) may be implemented as a specialized processing machine that includes hardware and/or software for performing the methods described herein. Accordingly, embodiments of the disclosure should not be construed as being limited to any particular operating environment, system architecture, or device or network configuration.

Operational Overview

Certain portions of the exemplary methods below will be described with reference to determining and communicating pre- and/or post-adjudication information to a service provider computer as part of the processing of a healthcare transaction. While the methods described below are described with reference to a healthcare claim transaction, each form of a healthcare transaction, such as a predetermination of benefits transaction, healthcare claim transaction, prescription claim or billing request, healthcare order transaction, or e-prescription transaction (e.g., electronic prescription order transaction, e-script, or e-prescription), should be individually read as being used in the methods described below.

Figure 2:
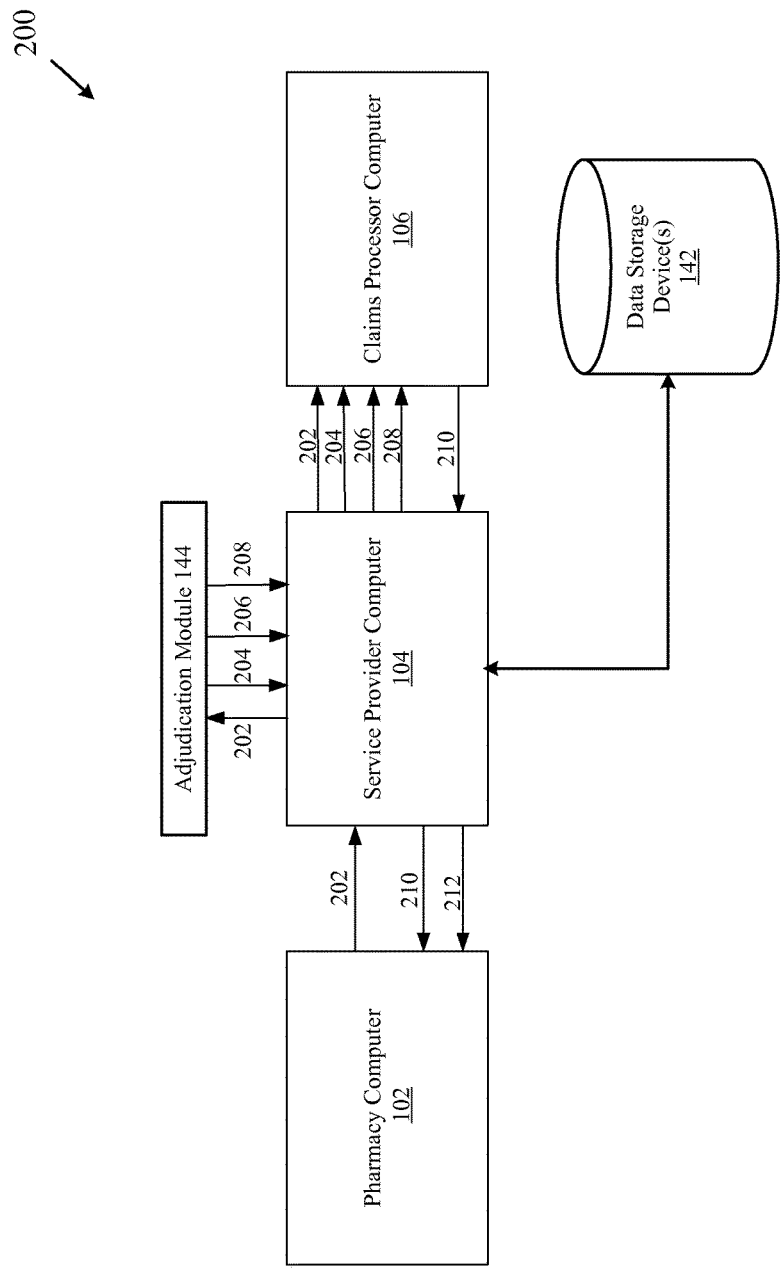
FIG. 2 illustrates an example block diagram for receiving, accessing, determining, and/or communicating proper pricing information and pre-/post-adjudication information associated with a medication and/or product as a part of the processing of a healthcare transaction submitted by a pharmacy computer, according to an example embodiment.
Figure 3:
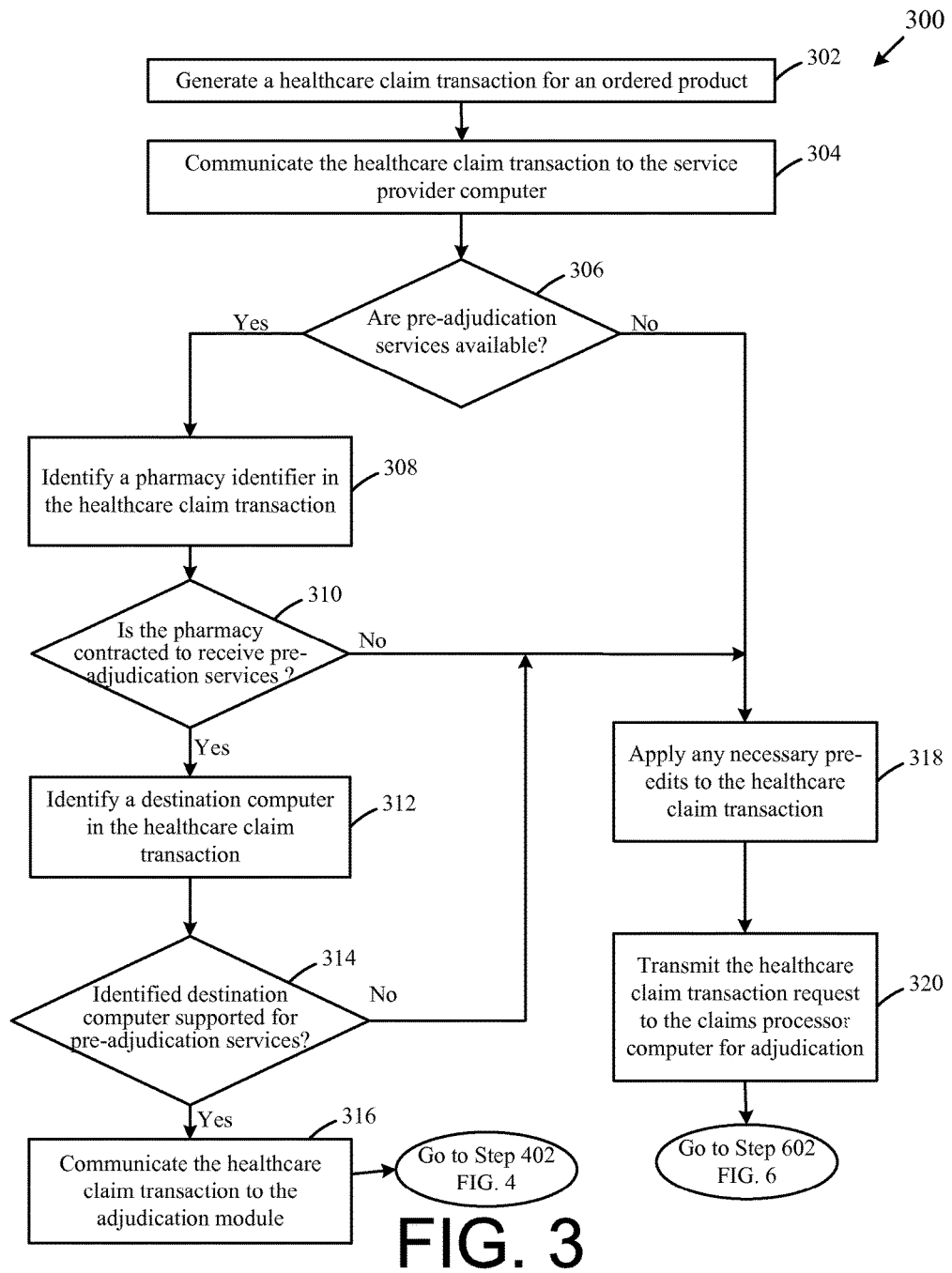
FIG. 3 illustrates a flow chart of an example method for determining whether there are pre-adjudication services available for a medication and/or product as a part of the processing of a healthcare transaction submitted by a pharmacy, according to an example embodiment.

FIG. 2 illustrates an example block diagram for receiving, accessing, determining, and/or communicating proper pricing information and pre- and/or post-adjudication information for a medication and/or product identified in a healthcare claim transaction as a part of the processing of the healthcare claim transaction submitted by a pharmacy computer, according to an example embodiment of the disclosure. FIG. 3 illustrates an example method 300 for determining whether there are pre-adjudication services available for a medication and/or product identified in the a healthcare claim transaction as a part of the processing of a healthcare claim transaction received from the pharmacy via the pharmacy computer 102, according to an example embodiment of the disclosure. The block diagram 200 of FIG. 2 will be discussed in conjunction with the method 300 of FIG. 3.

Referring now to FIGS. 1, 2, and 3, the exemplary method 300 begins at step 302, where a pharmacy computer, such as pharmacy computer 102, may generate a healthcare claim transaction 202 and transmit the healthcare claim transaction 202 to the service provider computer 104 via, for example, the network 108 at step 304. As an example, the healthcare claim transaction 202 may be in accordance with a version of a National Council for Prescription Drug Programs (NCPDP) Telecommunication Standard, although other standards may be utilized as well. As an example, the healthcare claim transaction 202 may include one or more the following information:

Payor ID/Routing Information
    Transaction Payor Identifier(s) that designates a destination of the healthcare claim transaction 202 (e.g., BIN Number, BIN Number and PCN, or BIN Number and Group ID)
Patient Information
    Name (e.g., Patient Last Name, Patient First Name, etc.)
    Date of Birth of Patient
    Age of Patient
    Patient Gender Code
    Patient Address (e.g., Street Address, City, State/Province, Zip/Postal Code, etc.)
    Patient Contact Information (e.g., patient telephone number, email address, etc.)
    Patient ID or other identifier (e.g., Health Insurance Claim Number (HICN), social security number, etc.)

Insurance/Coverage Information
    Cardholder Name (e.g., Cardholder First Name, Cardholder Last Name)
    Cardholder ID and/or other identifier (e.g., person code)
    Group ID and/or Group Information
    State payor information
Provider Information
    Prescriber Information
    Primary Care Provider ID or other identifier (e.g. National Provider Identifier (NPI) code)
    Primary Care Provider Name (e.g., Last Name, First Name)
    Prescriber ID or other identifier (e.g., NPI code, DEA number)
    Prescriber Name (e.g., Last Name, First Name)
    Prescriber Contact Information (e.g., Telephone Number)
    Pharmacy or other Healthcare Provider Information (e.g., store name, chain identifier, etc.)
    Pharmacy or other Healthcare Provider ID (e.g., NPI code)
Claim Information
    Medication, service, or product information (e.g., via NDC number or RxNorm code)
    Prescription/Service Reference Number
    Date Prescription Written
    Quantity Dispensed
    Days' Supply
    Diagnosis/Condition Code (e.g., International Classification of Diseases (ICD) code)
    Pricing information for the drug/service/product (e.g. network price, Usual & Customary price (U&C))
    Number of Refills Authorized
    One or more Drug Utilization Review (DUR) Codes
    Dispense as Written (DAW)/Product Selection Code At step 306, the service provider computer 104 may process the healthcare transaction 202. In one example, the processing of the healthcare transaction 202 may include, without limitation, determining whether there are pre-adjudication services (e.g., adjudication module 144), available. In one example implementation, pre-adjudication services may include determining whether one or more pharmacy pricing levels may be available for the medication or products identified in the corresponding healthcare transaction, such as healthcare claim transaction 202. The one or more pharmacy discounts may provide a patient a lower price for a medication and/or product identified in the healthcare claim transaction 202. If there are pre-adjudication services available, then the YES branch is followed and processing may proceed to step 308. If there are no pre-adjudication services available for the healthcare claim transaction 202, then the NO branch is followed and processing may continue to step 318.

At step 308, the service provider computer 104 may identify the pharmacy from which the healthcare claim transaction 202 was received. In one example, the service provider computer 104 may parse the received healthcare claim transaction 202 to identify a pharmacy identifier (e.g., a pharmacy name, NPI number, chain identifier, store number, etc.) in one or more fields of the healthcare claim transaction 202.

At step 310, the service provider computer 104 may further process the healthcare transaction. In one example, the processing of the healthcare transaction may include, without limitation, determining whether the pharmacy identified in the healthcare claim transaction 202 has contracted or otherwise agreed to receive the pricing verification service (e.g., a contracted pharmacy). In one example implementation, a contracted pharmacy may be a pharmacy or a member of a group of pharmacies associated with the healthcare claim transaction 202 (e.g., pharmacy chain) that has contracted with the service provider associated with the service provider computer 104 to receive the pricing verification service and other pre and/or post-adjudication services on medications and/or products requested in healthcare transactions and to thereby enable or activate the adjudication module 144 for use in processing healthcare transactions, like the healthcare claim transaction 202, that are routed or otherwise communicated to the service provider computer 104. For example, the service provider computer 104 may compare the identified pharmacy identifier (e.g., a pharmacy name, NPI code, pharmacy chain identifier, store number, etc.) to a list of pharmacy identifiers for those pharmacies that have contracted to enable or activate the adjudication module 144 to determine if a match exists. If a match exists, the pharmacy identified in the healthcare claim transaction 202 is determined to be a contracted pharmacy, the YES branch is followed, and processing may proceed to step 312. If a match is not identified, the pharmacy identified in the healthcare claim transaction 202 is not a contracted pharmacy, the NO branch is followed, and processing may proceed to step 318.

At step 312, processing of the healthcare claim transaction 202 may further include an identification of a corresponding claims processor computer 106 that is the destination for and/or will be adjudicating the healthcare claim transaction 202. In one example implementation, the service provider computer 104 may parse the healthcare claim transaction 202 to identify at least a transaction payor identifier (e.g., BIN Number, BIN Number and PCN, or BIN Number and Group ID).

At step 314, the service provider computer 104 may determine whether the identified claims processor computer 108 is supported by the system described in FIG. 1. In one non-limiting example, the service provider computer 104 may compare the identified transaction payor identifier to one or more tables within the data files 142. For example, the data files 142 may include one or more qualified claims processors data files. The service provider computer 104 may parse the one or more tables within the qualified claims processor data files to identify whether the transaction payor identifier matches a claims processor listed in the qualified claims processor files. If a match exists and the transaction payor identifier does exist in the claims processor files, the adjudication module 144 is determined to be activated for the current healthcare claim transaction 202, the YES branch is followed, and processing may proceed to step 316. If a match is not found and the transaction payor identifier does not exist in the qualified claims processor files, the adjudication module 144 is determined to not be available for the healthcare claim transaction 202, the NO branch is followed, and processing may proceed to step 318.

At step 316, the service provider computer 104 may route or deliver the healthcare claim transaction 202 to the adjudication module 144. In example embodiments where the adjudication module 144 is part of the service provider computer 104 or otherwise affiliated with the service provider computer 104, the delivery of the healthcare claim transaction 202 may be an internal delivery or an intra-network delivery. However, where the adjudication module 144 is a processor-based system distinct from the service provider computer 104, the delivery of the healthcare claim transaction 202 may be an external delivery, for example, via the network 108, according to an example embodiment of the disclosure. The process may then proceed to step 402 of FIG. 4.

If the service provider computer 104 does not employ the adjudication module 144, at step 318, the service provider computer 104 may perform one or more pre-edits on the healthcare claim transaction 202. At step 320, the service provider computer 104 may communicate the healthcare claim transaction 202 to the claims processor computer 106 for adjudication, as discussed herein, for example, in FIG. 6. The process proceeds to step 602 of FIG. 6.

Figure 4:
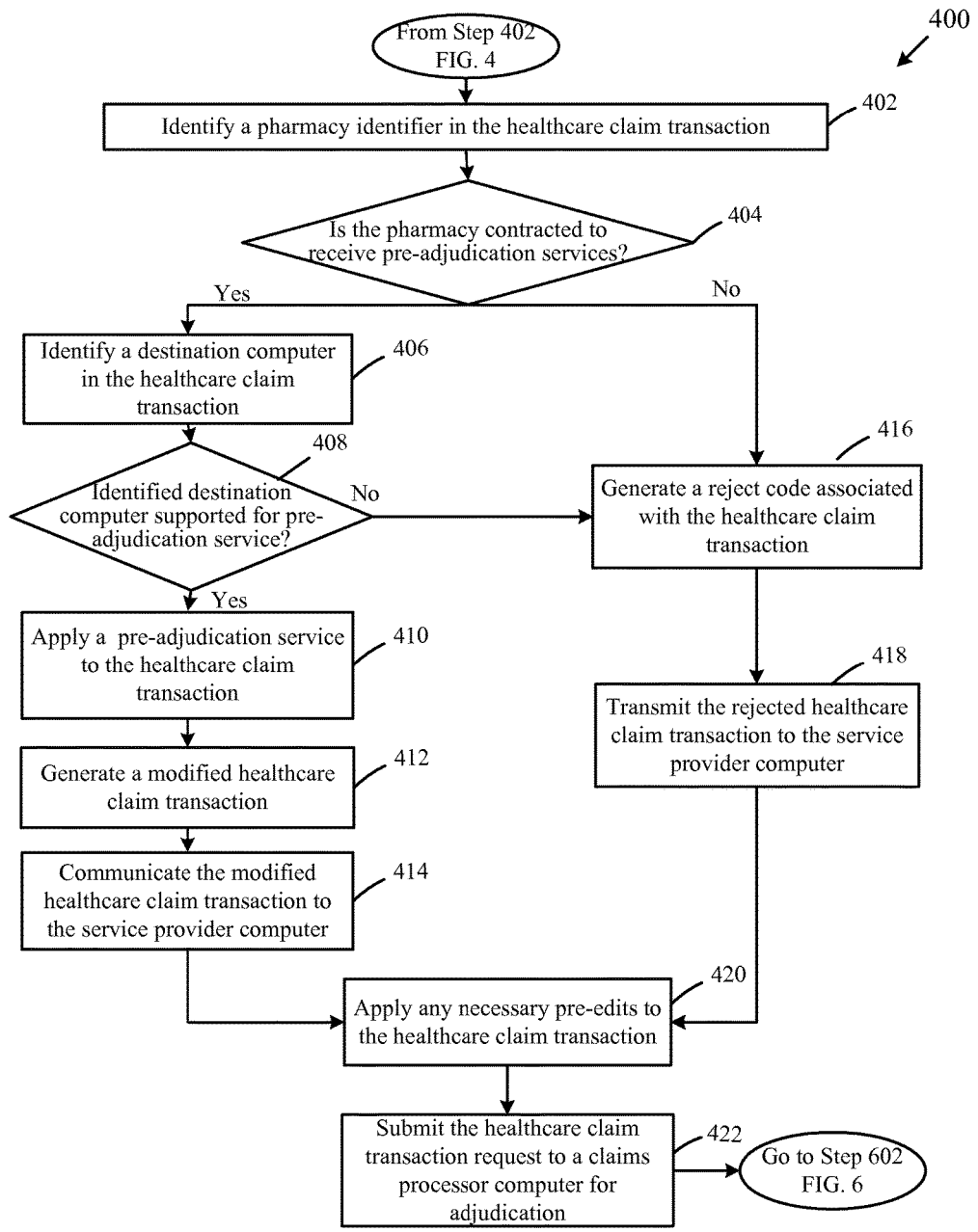
FIG. 4 illustrates a flow chart of an example method for receiving, accessing, determining, and/or communicating proper pricing information and other pre-adjudication information associated with a medication and/or product as a part of the processing of a healthcare transaction, according to an example embodiment.

FIG. 4 illustrates an example method 400 for receiving, accessing, determining, and/or communicating proper pricing information and other pre-adjudication information associated with a medication and/or product identified in a healthcare claim transaction 202 as a part of the processing of the healthcare claim transaction 202. The block diagram 200 of FIG. 2 will be discussed in conjunction with the method 400 of FIG. 4.

Referring now to FIGS. 1, 2, and 4, the exemplary method 400 begins at step 402, where the service provider computer 104 may identify a pharmacy identified in the healthcare claim transaction 202. In one example implementation, the service provider computer 104 may employ the adjudication module 144 to parse the received healthcare claim transaction 202 to identify a pharmacy identifier (e.g., a pharmacy name, NPI number, chain identifier, store number, etc.) in one or more fields of the healthcare claim transaction 202.

At step 404, the service provider computer 104 may further process the healthcare claim transaction 202. In one example implementation, the service provider computer 104 may employ the adjudication module 144 to determine whether the pharmacy identified by the pharmacy identifier in the healthcare claim transaction 202 is a contracted pharmacy. For example, the service provider computer 104 may employ the adjudication module 144 to compare the identified pharmacy identifier (e.g., a pharmacy name, NPI code, pharmacy chain identifier, etc.) to a list of acceptable pharmacy identifiers for those pharmacies that have contracted to enable or activate the adjudication module 144 to determine if a match exists. If a match exists, the pharmacy associated with the pharmacy computer 102 is determined to be contracted, the YES branch is followed and processing may proceed to step 406. If a match is not identified, the pharmacy associated with the pharmacy computer 102 is not contracted, the NO branch is followed and processing may proceed to step 416.

At step 406, processing of the healthcare transaction 202 may further include an identification of a corresponding claims processor computer 106. In one example implementation, the service provider computer 104 may employ the adjudication module 144 to parse the healthcare transaction 202 to identify at least a benefits provider identifier (e.g., BIN Number, BIN Number and PCN, or BIN Number and Group ID).

At step 408, the service provider computer 104 may determine whether the identified claims processor computer 108 is supported by the system described in FIG. 1. In one non-limiting example, the service provider computer 104 may employ the adjudication module 144 to compare the identified benefits provider identifier to one or more tables within the data files 142. For example, the data files 142 may include one or more qualified claims processors data files. The adjudication module 144 may parse the one or more tables within the qualified claims processor data files to identify whether the benefit provider identifier matches a claims processor listed in the qualified claims processor files. If the benefit identifier does exist in the qualified claims processor files, then the YES branch is followed and processing may proceed to step 410. If the benefit identifier does not exist in the qualified claims processor files, then the NO branch is followed and processing may proceed to step 416.

At step 410, the service provider computer 104 may apply pre-adjudication services to the healthcare transaction 202. In one example implementation, the service provider computer 104 may employ the adjudication module 144 to determine whether one or more pharmacy pricing levels (e.g., repricing information, pharmacy loyalty program and/or reward information, etc.) are available for the medication/product identified in the healthcare claim transaction 202.

At step 412, the service provider computer 104 may generate a modified healthcare claim transaction 204. In one example implementation, the service provider computer 104 may employ the adjudication module 144 to generate the modified healthcare claim transaction 204. The modified healthcare transaction 204 may include, without limitation, information included in the healthcare claim transaction 202 (e.g., medication identifiers, prescriber identifiers, patient identifiers, etc.) as well as additional and/or replacement information determined during the application of a pre-adjudication service at step 410. For example, if one or more one or more pricing levels were determined to exist for a corresponding medication and/or product identified in the healthcare transaction 202, the lower price may be substituted into the U&C field of the healthcare transaction 202. Further discussion of generating a modified healthcare transaction may be found in FIG. 5 of the disclosure.

At step 414, the adjudication module 144 may route or transmit the modified healthcare claim transaction 204 to the service provider computer 104. In example embodiments where the adjudication module 144 is part of the service provider computer 104 or otherwise affiliated with the service provider computer 104, the delivery of the modified healthcare claim transaction 204 may be an internal delivery or an intra-network delivery. However, where the adjudication module 144 is a processor-based system distinct from the service provider computer 104, the delivery of the modified healthcare claim transaction 204 may be an external transmission, for example, via the network 108, according to an example embodiment of the disclosure.

If the identified pharmacy in the healthcare claim transaction 202 is determined to not be a contracted pharmacy, and/or the claims processor is not a qualified claims processor, at step 416 a reject code identifying the basis for rejecting the healthcare claim transaction 202 and for insertion into the healthcare claim transaction 202 may be generated by the service provider computer 104. In one example implementation, the service provider computer 104 may employ the adjudication module 144 to generate a reject code that identifies the basis for rejecting the healthcare claim transaction 202 and for insertion into the healthcare claim transaction 202 without transmitting the healthcare claim transaction 202 to the claims processor computer 106 for adjudication. The reject code may include a message indicating one more reasons why the healthcare claim transaction 202 was rejected by the service provider computer 104 and/or the adjudication module 144. On the other hand, a separate message may be generated by the service provider computer 104 and/or the adjudication module 144 and inserted into another portion of the healthcare claim transaction 202. For example, the message can be a basis for the rejection, such as non-contracted pharmacy (e.g., NCP), and/or non-qualified claims process (e.g., NQCP), etc.

At step 418, the adjudication module 144 may route or deliver a rejected healthcare claim transaction 206 to the service provider computer 104. In example embodiments where the adjudication module 144 is part of the service provider computer 104 or otherwise affiliated with the service provider computer 104, the delivery of the rejected healthcare claim transaction 206 may be an internal delivery or an intra-network delivery. However, where the adjudication module 144 is a processor-based system distinct from the service provider computer 104, the transmission of the rejected healthcare claim transaction 206 may be an external delivery, for example, via the network 108, according to an example embodiment of the disclosure.

At step 420, the service provider computer 104 may perform one or more pre-edits on the modified healthcare claim transaction 204 or the rejected healthcare claim transaction 206. At step 422, the service provider computer 104 may transmit the modified healthcare claim transaction 204 to the claims processor computer 106 or the rejected healthcare claim transaction 206 to the pharmacy computer 102 for further processing, as discussed herein, for example, FIG. 6. The process may then proceed to step 602 of FIG. 6.

Figure 5:
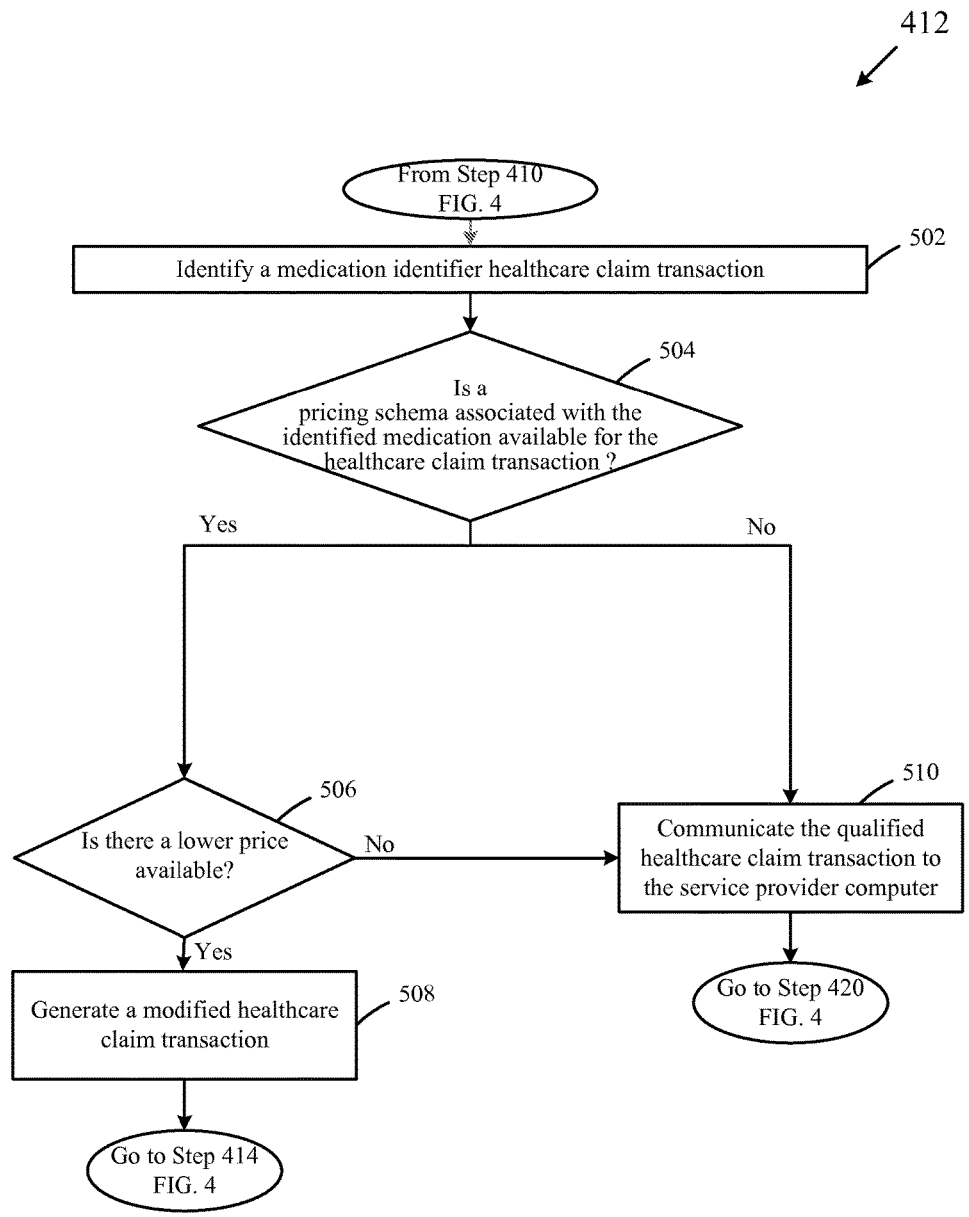
FIG. 5 illustrates a flow chart of an example method for determining and/or communicating pre-adjudication information associated with a pricing schema for a medication and/or product as a part of the processing of a healthcare transaction, according to an example embodiment.

FIG. 5 illustrates an example method 412 for determining and/or communicating pre-adjudication information associated with a pricing schema for a medication and/or product as a part of the processing of a healthcare transaction. The block diagram 200 of FIG. 2 will be discussed in conjunction with the method 412 of FIG. 5.

Referring now to FIGS. 1, 2, 4, and 5 the exemplary method 412 begins at step 502, where the service provider computer 104 may identify a medication identifier in the healthcare claim transaction 202. In one example implementation, the service provider computer 104 may employ the adjudication module 144 to parse the received healthcare claim transaction 202 to identify a medication identifier (e.g., NDC code, RxNorm code, medication name, etc.).

At step 504, the service provider computer 104 may determine whether a pricing schema exists for the identified medication and/or product in the healthcare claim transaction 202. In one example implementation, the service provider computer 104 may employ the adjudication module 144 to access one or more pricing schema data files. The adjudication module 144 may compare the identified medication and/or product identifier to identifiers for one or more medications and/or products within one or more pricing schema data files to determine if a match exists. In one example, the one or more pricing schema data files may be located in the database 142, and may be organized in one or more tables according to pharmacy, pharmacy chain, medication, and/or product identifiers. The one or more pricing schema data files may include pricing information for one or more medications and/or products for a pharmacy and/or a pharmacy chain. For example a pharmacy and/or pharmacy chain may offer one or more pricing levels to patients for certain medications and/or products. The differing pricing levels may occur, for example, based on whether or not a customer is a member of the particular pharmacy's loyalty program, pharmacy reward program, or the like. The pricing schema data files may be supplied by the pharmacy and/or pharmacy chain, and may be updated as new pricing becomes available. The pricing schema files may include medication information (e.g., medication identifier), retail price information for the corresponding pharmacy and/or pharmacy chain (e.g., U&C cost), one or more other pricing levels offered by the pharmacy and/or pharmacy chain, and a price for a medication and/or product corresponding to the one or more other pricing levels offered by the pharmacy and/or the pharmacy chain. As a non-limiting example, a pharmacy loyalty program may offer a patient one or more pricing levels for a medication and/or product identified in the healthcare claim transaction. For example, a pharmacy loyalty program may offer 10% off of every prescription filled at the pharmacy. Therefore, a pricing schema for pharmacy X, may include a retail price of $10.00 for medication X, a loyalty program offering 10% off of medication X, and a lower price of $9.00 for medication X. If the medication/product identifier in the healthcare claim transaction 202 matches a medication/product identifier for at least one of the pricing schema files, a determination is made that a pricing schema file exists for the identified medication and/or product in the healthcare claim transaction 202, and the YES branch is followed and processing may proceed to step 506. If a match does not exist, a determination is made that a pricing schema file does not exist for the identified medication and/or product in the healthcare claim transaction 202, and the NO branch is followed and processing may proceed to step 512.

At step 506, the service provider computer 104 may determine whether a lower cost is available for the identified medication and/or product in the healthcare claim transaction 202. In one example implementation, the service provider computer 104 may employ the adjudication module 144 to compare the cost identified in the U&C cost field in the healthcare claim transaction 202 (e.g, the U&C cost field in the healthcare claim transaction 202) for a medication and/or product with that of the one or more pricing levels for the same medication and/or product at that particular pharmacy in the one or more pricing schema files. For example, the service provider computer 104 may employ the adjudication module 144 to parse the one or more pricing schema files to locate and compare a cost identified in the healthcare claim transaction 202 (e.g, the U&C cost field in the healthcare claim transaction 202) for a medication and/or product with that of the one or more costs for the same medication and/or product in the matching one or more pricing schema files. In one non-limiting example, the healthcare claim transaction 202 may indicate that a medication and/or product has a U&C price of $20.00. The matching pricing schema files may indicate that the pharmacy has other pricing levels for that particular medication/product. One other pricing level for the particular medication/product is $18.00 while another is $22.00. The adjudication module 144 can compare the U&C price from the healthcare claim transaction 202 to the pricing levels in the matching pricing schema files to determine if any of the pricing levels in the matching pricing schema files is less than the U&C cost in the healthcare claim transaction 202. If, in one example, there are more than one pricing level lower than the U&C cost, the adjudication module 144 may compare the one or more pricing levels to determine which corresponds to the lowest price for the identified medication and/or product. If the adjudication module 144 determines that at least one pricing level is less than the U&C cost in the healthcare claim transaction 202, then the YES branch is followed and processing may proceed to step 508. On the other hand, if the adjudication module 144 determines that none of the pricing levels in the matching files is less than the U&C price in the healthcare claim transaction 202, for the identified medication and/or product, then the NO branch is followed and processing may proceed to step 510.

At step 508, the service provider computer 104 may generate a modified healthcare claim transaction 204. In one example implementation, the service provider computer 104 may employ the adjudication module 144 to generate a modified healthcare claim transaction 204 by removing the original U&C price in the healthcare claim transaction 202 and replacing it with the determined lower U&C price for the identified medication and/or product in the healthcare claim transaction 202. For example, the adjudication module 144 may locate the U&C price of the medication and/or product in the healthcare claim transaction 202, and replace the amount with the lowest medication and/or product U&C price identified in the pricing schema file(s) and offered by the pharmacy identified in the transaction 202. Alternatively, the adjudication module 144 may modify the healthcare transaction 202 to include both the U&C price listed in the healthcare claim transaction 202, as well as the determined lower price corresponding to a different pricing level for U&C pricing in the pricing schema file(s). The process may proceed to step 414 of FIG. 4.

If a pricing schema is not available for the identified medication and/or product in the healthcare claim transaction 202, or a lower U&C price is not available for the identified medication and/or product, then at step 510, a qualified healthcare claim transaction 208 may be communicated/transmitted by the adjudication module 144 to the service provider computer 104. In one example, the qualified healthcare claim transaction 208 may be eligible for additional pre-adjudication services or may be eligible for post-adjudication services, as discussed in FIG. 6 of this disclosure. In example embodiments where the adjudication module 144 is part of the service provider computer 104 or otherwise affiliated with the service provider computer 104, the delivery of the qualified healthcare claim transaction 208 may be an internal delivery or an intra-network delivery. However, where the adjudication module 144 is a processor-based system distinct from the service provider computer 104, the transmission of the qualified healthcare transaction 208 may be an external delivery, for example, via the network 108, according to an example embodiment of the disclosure. The process may proceed to step 420 of FIG. 4.

Figure 6:
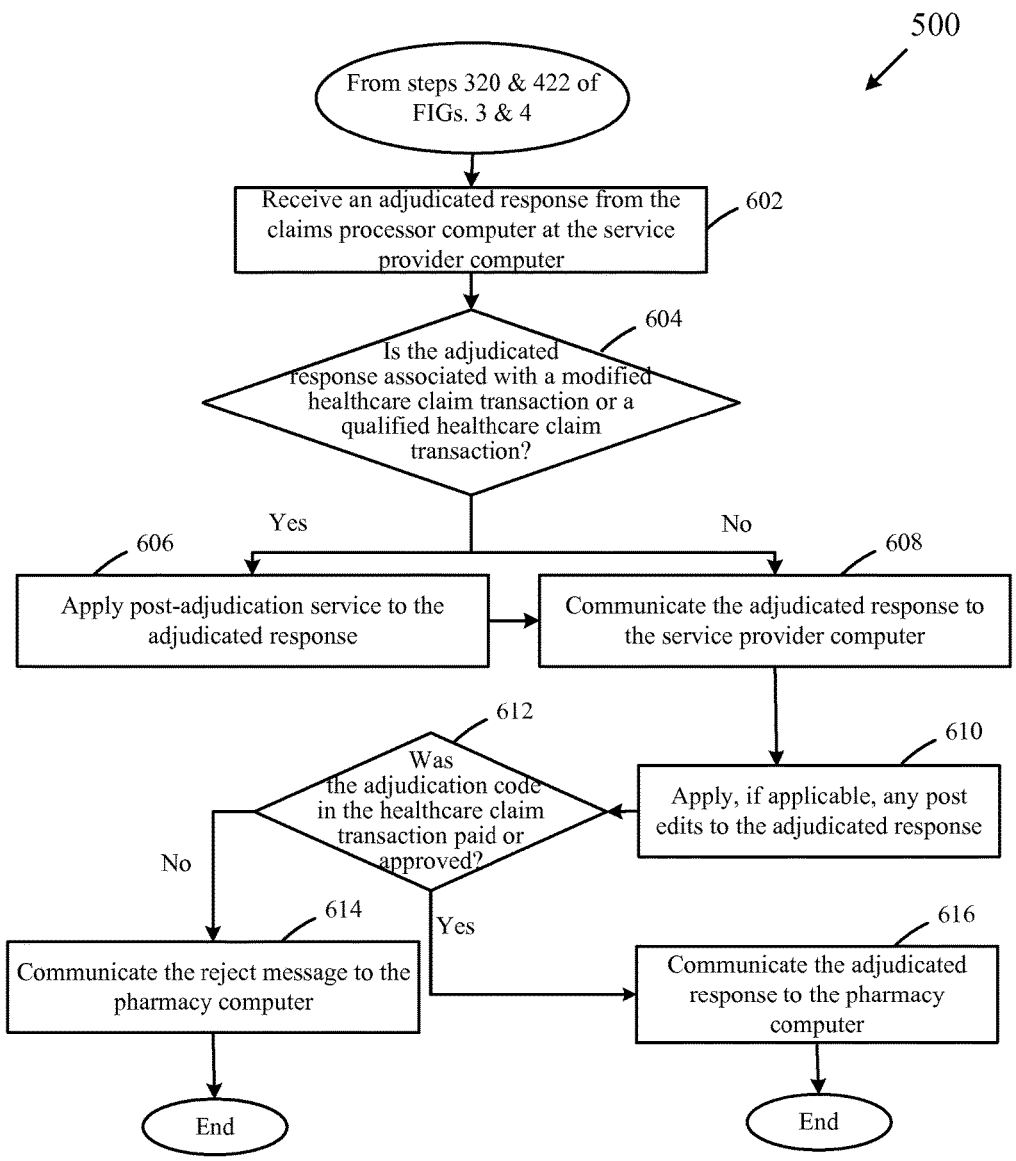
FIG. 6 illustrates a flow chart of an example method for determining and/or communicating proper pricing information and other post-adjudication information associated with a medication and/or product as a part of the processing of a healthcare transaction, according to an example embodiment.

FIG. 6 is a flow chart illustrating an example method 600 for determining and/or communicating proper pricing information and other post-adjudication information associated with a medication and/or product identified in a healthcare claim transaction and as a part of the processing of the healthcare claim transaction. The block diagram 200 of FIG. 2 will be discussed in conjunction with the method 600 of FIG. 6.

Referring now to FIGS. 1, 2, and 6 the exemplary method 600 begins at step 602, where the service provider computer 104 may receive an adjudicated claim transaction response 210 from the claims processor computer 106. The adjudicated claim transaction response may include, without limitation, an adjudication indicator enabling the service provider computer 104 to identify the adjudicated response 210 as a response associated with a modified healthcare claim transaction 204 or a qualified healthcare claim transaction 208. For example, without limitation, the adjudicated claim transaction response 210 may include a status indicator "AMQ", or adjudication module qualified. The service provider computer 104 can identify the status indicator and determine based on that status indicator (such as by, for example, comparing the status indicator to a table or schedule of status indicators and corresponding descriptions to identify a match) that the adjudication module 144 invoked a change to the modified healthcare claim transaction 204. Based on the determination that the identification of the status indicator that signals a change was invoked, the service provider computer 104 can store a copy of all or a portion of the modified healthcare claim transaction 204, the qualified healthcare claim transaction 208, and/or the adjudicated response 210 in, for example, the database 142. Alternatively and/or additionally, the service provider computer 104 may employ the adjudication module 144 to track the modified healthcare claim transaction 204 and/or the qualified healthcare claim transaction 208, such that the adjudicated response 210 is identified as corresponding to either the modified healthcare transaction 204 and/or the qualified healthcare transaction 208.

If the adjudicated response 210 is identified as corresponding to a modified healthcare transaction 204 and/or a qualified healthcare transaction 208 (e.g., includes the status indicator "AMQ" and/or some other tracking identification), the service provider computer 104 may employ the adjudication module 144 to apply any post-adjudication logic to the adjudicated claim transaction response 210. For example, the post-adjudication logic may include capturing information associated with one or more fields included in the adjudicated claim transaction response 210 for further processing by the adjudication module 144. In addition, post-adjudication logic may include, but is not limited to measuring an adherence level (e.g., how closely is the patient following a prescribed regimen for a medication or product) for a patient taking a medication or product or receiving a service, modifying pricing response fields in the adjudicated claim transaction response 210 based on pricing schema defined by claims processors or other third-parties, inserting messages into fields of the adjudicated claim transaction response 210 via free text or codes (e.g., coupons available for subsequent transactions by the customer), and monitoring compliance of the claims processor associated with the claims processor computer 106 to contractual terms, such as medication/product pricing.

At step 608, the adjudicated claim transaction response 210 may be communicated to the service provider computer 104. In example embodiments where the adjudication module 144 is part of the service provider computer 104 or otherwise affiliated with the service provider computer 104, the delivery of the adjudicated claim transaction response 210 may be an internal delivery or an intra-network delivery. However, where the adjudication module 144 is a processor-based system distinct from the service provider computer 104, the transmission of the adjudicated claim transaction response 210 may be an external delivery, for example, via the network 108, according to an example embodiment of the disclosure.

The adjudicated claim transaction response 210 may also include, without limitation, a transaction status indicator for the healthcare transaction (e.g., the healthcare claim transaction 202, modified healthcare claim transaction 204, rejected healthcare claim transaction 206, or qualified healthcare claim transaction 208). In certain example embodiments, the transaction status indicator is a code in a field of the healthcare transaction that indicates whether the healthcare transaction was paid/approved or rejected. In one example implementation, when the adjudication for the healthcare claim transaction is paid, the adjudicated claim transaction response 210 may have a transaction status indicator "P". If, however, the healthcare claim transaction is rejected, the adjudicated claim transaction response 210 may have a transaction indicator "R".

At step 610, the service provider computer 104 may perform any post-edits on the adjudicated response 210. At step 612, the service provider computer 104 may determine whether the adjudication for the healthcare claim transaction was paid or rejected by parsing the transaction and evaluating the transaction status indicator. If the adjudicated claim transaction response 210 includes a transaction status indicator that indicates that the healthcare claim transaction was rejected, then the NO branch is followed and processing may proceed to step 614. If the adjudicated claim transaction response 210 includes a transaction status indicator that indicates that the healthcare claim transaction was paid, then the YES branch is followed and processing may proceed to step 616.

If the adjudicated claim transaction response 210 includes the transaction status indicator "R", at step 614, the service provider computer may communicate the adjudicated claim transaction response 210 as a part of a reject message 212 to the pharmacy computer 102. The reject message may include one or more rejection reasons corresponding to the healthcare claim. transaction (e.g., healthcare claim transaction 202, modified healthcare claim transaction 204, rejected healthcare claim transaction 206, or qualified healthcare claim transaction 208), and/or one or more reject codes. The process may end after step 614.

If the adjudicated claim transaction response 210 includes the transaction status indicator "P", at step 616, the service provider computer 104 may transmit the adjudicated claim transaction response 210 to the pharmacy computer 102 via, for example, the network 108. The process may end after step 616.

Accordingly, example embodiments disclosed herein can provide the technical effects of creating a system and methods that provide a real-time or near real time way to determine and communicate proper product pricing information and other pre-/post-adjudication information as part of the processing of a healthcare transaction received from a pharmacy computer associated with a pharmacy including, but not limited to, comparing one or more pharmacy pricing schema with the U&C price listed in the healthcare transaction for the product/medication identified in the healthcare transaction to determine whether a lower U&C price is offered by the pharmacy for the product/medication. In this regard, pharmacies and other healthcare providers are more likely to comply with state mandated regulations to provide the consumer with the lowest price available for the medication/product. While the exemplary embodiments described herein disclose certain steps occurring at the service provider computer 104 and/or the adjudication module 144, in alternative embodiments those steps described with reference to FIGS. 1-6 may alternately be completed at the healthcare provider computer 102, a processor driven device separate and distinct from the healthcare provider computer 102 and the service provider computer 104, and/or any combination of those devices along with the service provider computer 104. In those alternate embodiments, certain transmission/receiving steps described above with reference to FIGS. 1-6 may be omitted while others may be added, as understood by one of ordinary skill in the art. The intent being that in alternate embodiments, any of the devices/computers discussed in FIG. 1 are capable of completing any or any part of the methods described with reference to FIGS. 2-6.

Various block and/or flow diagrams of systems and methods and/or computer program products according to example embodiments are described above. It will be understood that one or more blocks of the block diagrams and flow diagrams, and combinations of blocks in the block diagrams and flow diagrams, respectively, can be implemented by computer-executable program instructions. Likewise, some blocks of the block diagrams and flow diagrams may not necessarily need to be performed in the order presented, or may not necessarily need to be performed at all, according to some embodiments.

These computer-executable program instructions may be loaded onto a special purpose computer or other particular machine, a processor, or other programmable data processing apparatus to produce a particular machine, such that the instructions that execute on the computer, processor, or other programmable data processing apparatus create means for implementing one or more functions specified in the flowchart block or blocks. These computer program instructions may also be stored in a computer-readable memory that can direct a computer or other programmable data processing apparatus to function in a particular manner, such that the instructions stored in the computer-readable memory produce an article of manufacture including instruction means that implement one or more functions specified in the flow diagram block or blocks. As an example, embodiments disclosed herein may provide for a computer program product, that includes a computer usable medium having a computer-readable program code or program instructions embodied therein, said computer-readable program code adapted to be executed to implement one or more functions specified in the flow diagram step or steps. The computer program instructions may also be loaded onto a computer or other programmable data processing apparatus to cause a series of operational elements or steps to be performed on the computer or other programmable apparatus to produce a computer-implemented process such that the instructions that execute on the computer or other programmable apparatus provide elements or steps for implementing the functions specified in the flow diagram step or steps.

Accordingly, blocks of the block diagrams and flow diagrams support combinations of means for performing the specified functions, combinations of elements or steps for performing the specified functions and program instruction means for performing the specified functions. It will also be understood that each block of the block diagrams and flow diagrams, and combinations of blocks in the block diagrams and flow diagrams, can be implemented by special-purpose, hardware-based computer systems that perform the specified functions, elements or steps, or combinations of special purpose hardware and computer instructions.

Many modifications and other embodiments of those set forth herein will be apparent having the benefit of the teachings presented in the foregoing descriptions and the associated drawings. Therefore, it is to be understood that the disclosure is not to be limited to the specific embodiments disclosed and that modifications and other embodiments are intended to be included within the scope of the appended claims. Although specific terms are employed herein, they are used in a generic and descriptive sense only and not for purposes of limitation.

That which is claimed is:

1. A computer-implemented method comprising:
   receiving, by one or more computers operating as a service provider in a network, and from a pharmacy computer associated with a pharmacy and operative in the network, a prescription claim request communicated via respective network interfaces of the pharmacy computer and the one or more computers, wherein the network interfaces are communicatively connected to respective memory devices and processors of the one or more computers operating as the service provider, and the pharmacy computer, wherein the prescription claim request identifies at least (a) a product identifier for a prescribed product, Q) a pharmacy identifier for the pharmacy, (c) a claims processor identifier identifying a claims processor computer operative in the network and remote from the pharmacy computer and service provider, and (d) a usual and customary cost corresponding to the prescribed product established by the pharmacy;
   determining, by the at least processor of the one or more computers, that at least one pre-adjudication service associated with the one or more computers is available for the prescribed product;
   accessing on a database, via the network interface of the one or more computers, one or more data files comprising at least a pricing schema file for the identified pharmacy, wherein the pricing schema file comprises a cost to the identified pharmacy to acquire the prescribed product;
   determining, by processing the pricing schema file with at least the processor of the one or more computers, that a price, lower than the usual and customary cost, is available at the pharmacy for the prescribed product identified in the prescription claim request, the lower price being available due to at least a pharmacy loyalty program or a pharmacy reward program established by the pricing schema for the identified pharmacy, wherein the pricing schema includes a cost to the pharmacy to acquire the prescribed product and pharmacy level discount information including at least one of the pharmacy loyalty program or the pharmacy reward program;
   generating, by at least the processor of the one or more computers, a modified prescription claim request by replacing the cost of the prescribed product in the prescription claim request with the lower price for the prescribed product;
   transmitting, via the network interface of the one or more computers, the modified prescription claim request to the claims processor computer for a benefits adjudication;
   receiving, via the network interface of the one or more computers, an approved adjudicated response to the modified prescription claim request;
   transmitting, via the network interface of the one or more computers to the pharmacy computer, the approved adjudicated response; and
   causing the pricing schema file to be updated on the database via the network interface of the pharmacy computer as new pricing data becomes available, wherein the one or more computers operating as the service provider retrieves real-time or near real-time pricing data maintained by the pharmacy computer.

2. The computer-implemented method of claim 1 wherein the determining, by the one or more computers, that a lower price is available for the prescribed product identified in the prescription claim request comprises:
   identifying, by the one or more computers, a corresponding product identifier in the pricing schema file and;
   determining, by the one or more computers, that one or more pharmacy pricing levels are available for the corresponding product identifier; and
   comparing, by the one or more computers, the one or more pharmacy pricing levels available for the corresponding product identifier with the cost corresponding to the prescribed product.

3. The computer-implemented method of claim 1, wherein the one or more data files further include at least one of an eligibility verification file or a formulary design file.

4. The computer-implemented method of claim 3 further comprising:
determining, by the one or more computers, that another pre-adjudication service is available for the prescription claim request, wherein the pre-adjudication service may include medication therapy management accessible in the formulary design file.

5. The computer-implemented method of claim 1, wherein the cost corresponding to the product in the prescription claim request is a price for the product established by a pharmacy associated with the pharmacy system and is a usual and customary price.

6. The computer-implemented method of claim 1, wherein the determining, by the one or more computers, that a pre-adjudication service is available for the prescribed product comprises:
determining that the pharmacy is an eligible pharmacy by comparing the pharmacy identifier with one or more pharmacies contracted with the service provider to receive one or more pre-adjudication services; and
determining that the claims processor associated with the claims processor computer is an eligible payer by comparing the claims processor identifier with one or more claims processor computers qualified by the one or more computers to receive one or more pre-adjudication services.

7. The computer-implemented method of claim 1 further comprising: determining, by the one or more computers, that at least one post adjudication service is available for the approved adjudicated response; and
performing, by the one or more computers, the at least one post-adjudication service to the approved adjudicated response, wherein the approved adjudicated response transmitted to the pharmacy computer includes a modification or result of the post-adjudication service.

8. The computer-implemented method of claim 1 further comprising:
generating, by the one or more computers, a modification report comprising one or more modifications made to the prescription claim request or the approved adjudicated response; and
transmitting, by the one or more computers to the pharmacy computers, the modification report.

9. A system comprising:
at least one memory operable to store computer-executable instructions;
a network interface configured for facilitating communication in a network between at least a service provider, a pharmacy computer, and a database; and
at least one processor operating as the service provider in the network, and configured to access the at least one memory and execute the computer-executable instructions to:
receive a prescription claim request via at least the pharmacy computer associated with a pharmacy operative in the network, wherein the prescription claim request identifies at least (a) a product identifier for a prescribed product, (b) a pharmacy identifier for the pharmacy, (c) a claims processor identifier identifying a claims processor computer operative in the network and remote from the pharmacy computer and service provider, and (d) a usual and customary cost corresponding to the prescribed product established by the pharmacy;
determine, by the at least one processor operating as the service provider, that an adjudication platform associated with the at least one processor is available for the prescribed product;
determine that an adjudication platform associated with the one or more computers is available for the prescribed product;
access on the dataset via the network interface of the one or more computers, one or more data files comprising at least a pricing schema file for the identified pharmacy, wherein the pricing schema file comprises a cost to the identified pharmacy to acquire the prescribed product;
determine by processing the pricing schema file with at least the processor of the one or more computers that a price, lower than the usual and customary cost, is available at the pharmacy for the prescribed product identified in the prescription claim request, the lower price being available due to at least a pharmacy loyalty program or a pharmacy reward program established by the pricing schema for the identified pharmacy, wherein the pricing schema includes a cost to the pharmacy to acquire the prescribed product and pharmacy level discount information including at least one of the pharmacy loyalty program or the pharmacy reward program;
generate by at least the processor of the one or more computers, a modified prescription claim request by replacing the cost of the prescribed product in the prescription claim request with the lower price for the prescribed product;
transmit via the network interface of the one or more computers the modified prescription claim request to the claims processor computer for a benefits adjudication;
receive via the network interface of the one or more computers an approved adjudicated response to the modified prescription claim request;
transmit, via the network interface of the one or more computers to the pharmacy computer, the approved adjudicated response; and
cause the pricing schema file to be updated on the database via the network interface of the pharmacy computer as new pricing data becomes available, wherein the one or more computers operating as the service provider retrieves real-time or near real-time pricing data maintained by the pharmacy computer.

10. The system of claim 9, wherein the at least one or more processors
configured to execute the computer-executable instructions to determine that a lower price is available for the prescribed product identified in the prescription claim request are further configured to:
identify a corresponding product identifier in the pricing schema file and;
determine that one or more pharmacy pricing levels are available for the corresponding product identifier; and
compare the one or more pharmacy pricing levels available for the corresponding product identifier with the cost corresponding to the prescribed product.

11. The system of claim 9, wherein the one or more data files further include at least one of an eligibility verification file or a formulary design file.

12. The system of claim 11, wherein the at least one or more processors are further configured to execute the computer-executable instruction to:

determine that another pre-adjudication service is available for the prescription claim request, wherein the pre-adjudication service may include medication therapy management accessible in the formulary design file.

13. The computer-implemented method of claim 9, wherein the cost corresponding to the product in the prescription claim request is a price for the product established by a pharmacy associated with the pharmacy system and is a usual and customary price.

14. The system of claim 9, wherein the at least one or more processors are further configured to execute the computer-executable instruction to:
  determine that at least one post adjudication service is available for the approved adjudicated response; and
  perform the at least one post adjudication service to the approved adjudicated response, wherein the approved adjudicated response transmitted to the pharmacy computer includes a modification or result of the post-adjudication service.

15. The system of claim 9, wherein the at least one or more processors are further configured to execute the computer-executable instruction to:
  generate a modification report comprising one or more modifications made to the prescription claim request or the approved adjudicated response; and
  transmit to the pharmacy computers, the modification report.

16. The computer-implemented method of claim 9, wherein the at least
  one or more processors configured to execute the computer-executable instructions to determine that a pre-adjudication service is available for the prescribed product is further configured to:
    determine that the pharmacy is an eligible pharmacy by comparing the pharmacy identifier with one or more pharmacies contracted with the service provider to receive one or more pre-adjudication services; and
    determine that the claims processor associated with the claims processor computer is an eligible payer by comparing the claims processor identifier with one or more claims processor computers qualified by the one or more computers to receive one or more pre-adjudication services.

* * * * *

UNITED STATES PATENT AND TRADEMARK OFFICE
CERTIFICATE OF CORRECTION

| | |
|---|---|
| PATENT NO. | : 10,713,694 B1 |
| APPLICATION NO. | : 14/466995 |
| DATED | : July 14, 2020 |
| INVENTOR(S) | : Harris et al. |

Page 1 of 1

It is certified that error appears in the above-identified patent and that said Letters Patent is hereby corrected as shown below:

In the Claims

<u>Column 21,</u>
Line 67, "Q)" should read --(b)--.

Signed and Sealed this
Twenty-fifth Day of August, 2020

Andrei Iancu
*Director of the United States Patent and Trademark Office*